(12) United States Patent
Schäfer et al.

(10) Patent No.: US 10,337,724 B2
(45) Date of Patent: Jul. 2, 2019

(54) MACHINE FOR EXTRACORPOREAL BLOOD TREATMENT COMPRISING LIGHT-EMITTING UNIT

(71) Applicant: B. BRAUN AVITUM AG, Melsungen (DE)

(72) Inventors: Oliver Schäfer, Neuenstein (DE); Christian Schleicher, Dipperz (DE); Dirk Möller, Altmorschen (DE)

(73) Assignee: B. Braun Avitum AG (DE)

( * ) Notice: Subject to any disclaimer, the term of this patent is extended or adjusted under 35 U.S.C. 154(b) by 184 days.

(21) Appl. No.: 15/415,016

(22) Filed: Jan. 25, 2017

(65) Prior Publication Data
US 2017/0234524 A1    Aug. 17, 2017

(30) Foreign Application Priority Data

Feb. 11, 2016   (DE) ...................... 10 2016 102 353

(51) Int. Cl.
*F21V 33/00*      (2006.01)
*A61M 1/16*      (2006.01)
(Continued)

(52) U.S. Cl.
CPC ........... *F21V 33/0068* (2013.01); *A61M 1/14* (2013.01); *A61M 1/1621* (2014.02); *G02B 6/001* (2013.01); *G02B 6/0008* (2013.01); *A61M 2205/18* (2013.01); *A61M 2205/502* (2013.01); *A61M 2205/583* (2013.01); *A61M 2205/587* (2013.01);
(Continued)

(58) Field of Classification Search
None
See application file for complete search history.

(56) References Cited

U.S. PATENT DOCUMENTS

| | | | | |
|---|---|---|---|---|
| 4,925,299 A | * | 5/1990 | Meisberger | G01J 1/16 356/40 |
| 9,220,832 B2 | * | 12/2015 | Weaver | A61M 1/3627 |

(Continued)

FOREIGN PATENT DOCUMENTS

| | | |
|---|---|---|
| DE | 29805006 U1 | 5/1998 |
| DE | 10 2013 005 743 | 10/2014 |
| EP | 2371411 A1 | 10/2011 |

OTHER PUBLICATIONS

European Search Report for EP Application No. 17153376.3, dated Jun. 19, 2017 with translation, 12 pages.
German Search Report (with translation) for DE 10 2016 102 353.1 dated Jul. 29, 2016.

*Primary Examiner* — Chester T Barry
(74) *Attorney, Agent, or Firm* — RatnerPrestia

(57) ABSTRACT

A machine for extracorporeal blood treatment including a housing for accommodating operational components of the machine for extracorporeal blood treatment and a light-emitting unit having no diffusion disk for displaying an operating and/or therapy condition of the machine according to the principle of ambient light. The light-emitting unit is arranged in a predetermined sequence and/or with predetermined shaping on at least one portion of the housing. The light-emitting unit is a flexible light conductor having at least one end-face light coupling surface at a first end and at least one end-face light output surface at a second end or alternatively a self-luminous flat and/or flexible OLED unit.

12 Claims, 3 Drawing Sheets

(51) Int. Cl.
  *F21V 8/00*    (2006.01)
  *A61M 1/14*    (2006.01)
  *F21Y 113/13*  (2016.01)
  *F21Y 115/10*  (2016.01)
  *F21Y 115/15*  (2016.01)
  *F21W 111/00*  (2006.01)
  *F21W 131/20*  (2006.01)
  *F21Y 105/00*  (2016.01)

(52) U.S. Cl.
  CPC ...... *F21W 2111/00* (2013.01); *F21W 2131/20* (2013.01); *F21Y 2105/00* (2013.01); *F21Y 2113/13* (2016.08); *F21Y 2115/10* (2016.08); *F21Y 2115/15* (2016.08)

(56) References Cited

U.S. PATENT DOCUMENTS

| | | | |
|---|---|---|---|
| 2003/0086817 A1 | 5/2003 | Horton, III | |
| 2012/0170304 A1 | 7/2012 | Purfuerst et al. | |
| 2013/0193041 A1* | 8/2013 | Rohde | A61M 5/44 210/143 |
| 2014/0230071 A1* | 8/2014 | Adam | G06F 21/60 726/26 |
| 2014/0252926 A1* | 9/2014 | Schaefer | A61M 1/14 312/209 |
| 2015/0238717 A1* | 8/2015 | Hatanaka | A61M 1/1086 700/90 |
| 2016/0055303 A1* | 2/2016 | Keller | G06F 19/3406 705/2 |
| 2017/0173251 A1* | 6/2017 | Doyle | A61M 1/1629 |

* cited by examiner

MACHINE FOR EXTRACORPOREAL BLOOD TREATMENT COMPRISING LIGHT-EMITTING UNIT

CROSS REFERENCE TO RELATED APPLICATIONS

This application claims priority to German application DE 10 2016 102 353.1 filed Feb. 11, 2016, the contents of such application being incorporated by reference herein.

FIELD OF THE INVENTION

The invention relates to a machine for extracorporeal blood treatment comprising a light-emitting unit and relates especially to a machine for extracorporeal blood treatment which includes an illumination system as light-emitting unit for displaying an operating condition, for generating ambient light, room illumination and/or the like.

BACKGROUND OF THE INVENTION

Machines for extracorporeal blood treatment such as dialyzers frequently include luminaires which may be polychromatic or may be designed to produce plural colors such as light-emitting diodes or LED, for example. Such luminaires usually are arranged to irradiate, depending on the status or operating condition of the machine (red, yellow, green), onto a transparent diffusion disk so as to generate a luminous field which marks a respective operating condition to be visible from outside. Further, the principle of a beacon light based on light-emitting diodes and operating with a diffusion disk is known.

It is a drawback in this context, inter alia, that the luminaires have to be arranged directly behind the diffusion disk so as to irradiate their light outside the machine for extracorporeal blood treatment and that, for this purpose, appropriate space is required exactly at that position and electrical wires have to laid there, for example.

The luminaires illuminate merely punctual at their mounting location. For a larger surface to be illuminated or for luminous graphics an appropriately large number of luminaires involving appropriately large space and complex wiring and controlling is required. Nevertheless, in this way desired luminous density or light intensity and/or sufficiently uniform light emission or light distribution cannot be achieved in a satisfactory manner and repair works are complicated in the case of failure of individual luminaires.

In practice moreover during dialysis therapy a dialyzer is preferably placed in the vicinity of or adjacent to a patient. The dialyzer regularly includes an operating panel for controlling the machine via which also various pieces of information may be available. Such operating panel and the information display thereof usually have a complex and/or detailed design and, otherwise, need not necessarily be facing a patient, for example.

Therefore, a separate and quickly detectable display, reporting or feedback of an operating and/or therapy state may improve and accelerate the perception of the user and/or the patient relevant in this respect, in particular as not every person involved in therapy or every patient can be expected to be able to correctly or quickly detect complex information on the operating panel.

SUMMARY OF THE INVENTION

Consequently, the object underlying the invention is to provide a machine for extracorporeal blood treatment comprising a light-emitting unit which increases light-related degrees of freedom for displaying states of the dialyzer and/or of a course of therapy outside an operating panel and/or display of information thereon.

This object is achieved, according to aspects of the invention, by a machine for extracorporeal blood treatment comprising the features of the independent claim. Advantageous further developments of the invention are the subject matter of the enclosed subclaims.

The invention is based, as general idea, on guiding light from a light source such as, for example, a light-emitting diode or, respectively, LED or OLED to any or a desired location of the machine for extracorporeal blood treatment and emitting, i.e. irradiating the same at such location.

In one embodiment, a light conductor which may be made from transparent material may be provided for this purpose. In this case the light conductor may partly emit light at a predetermined location or the entire light conductor may emit light and in this way form a light-emitting unit (luminaire) radiating at least partly on its periphery up to radiating all around. In the case of a beaconing characteristic the light conductor may be used, for example, as a 360° status display visible and detectable from all directions and/or a luminaire producing ambient light according to the ambient air principle which projects a therapy condition or an operating condition of the dialyzer onto any surface in the environment of the dialyzer and thus may improve the user's perception.

In another embodiment, the light-emitting unit and, respectively, the light conductor may be formed by a self-luminous OLED (Organic Light Emitting Diode) arrangement and may be disposed to display information such as an operating condition of the machine or a therapy condition by being placed on any or a predetermined visible apparatus surface. Based on the characteristics of OLED technology, on the one hand, an OLED unit in total, i.e. the entire OLED, may emit light and thus may be used as a 360° status display, and/or, on the other hand, may be used to guide light to any location of the machine. Depending on the geometric or flat design of the light-emitting unit used (light conductor and/or OLED unit), for instance part of or else the entire machine surface may light up so that e.g. a light conductor/an OLED unit corresponding to a peripheral housing contour, a partial illumination by a laterally peripheral light conductor/laterally extending OLED unit and/or a flat light conductor/a flat OLED unit corresponding to a monitor or housing surface can be realized.

The invention is advantageous especially to the effect that a light source need not be provided directly behind a diffusion disk, but may be arranged, depending on the space available, at any position inside the apparatus or as a self-luminous surface at a predetermined position on the apparatus. In this way, also positions on the dialyzer which have not been reached so far due to a lack of space available there, for example, may be configured to be light-emitting. Hence, related to development, the invention increases degrees of freedom and easily achieves improved legibility and visibility of a machine status for a user.

In detail, the afore-mentioned advantages are realized and the object is achieved by a machine for extracorporeal blood treatment comprising at least one housing forming part of this machine for extracorporeal blood treatment for accommodating operational components of the machine for extracorporeal blood treatment; and/or a light-emitting unit having no diffusion disk for displaying an operating and/or therapy condition of the machine for extracorporeal blood treatment according to the principle of ambient light, with the light-emitting unit being arranged in a predetermined sequence and/or with predetermined shaping on at least one portion of the housing and is a flexible light conductor (LLa to LLe) which includes at least one end-face light coupling surface at a first end and at least one end-face light output surface at a second end.

Advantageously, in this way a light-generating element such as, for example, a LED may be arranged distant from a desired light output location in a space that can be properly used there and the light thereof can be guided via the light conductor to the desired light output location.

Preferably, the flexible light conductor includes at least one portion coupling out light in the radial direction along its longitudinal extension. Of advantage, for this purpose the light conductor may be configured (processed) so that it couples out light on at least one predetermined location and/or in a predetermined direction up to radially beaconing of the light conductor.

Preferably the light-emitting unit is arranged in order to project a therapy condition and/or an operating condition of the machine for extracorporeal blood treatment with ambient light onto a surface in the environment of this machine. Advantageously, the light intensity to be achieved by the light-emitting unit is such that at least the environment of the machine for extracorporeal blood treatment can be lightened and/or such that a therapy condition and/or operating condition are visible on a surface in space lightened by the light-emitting unit.

Alternatively preferred, the light-emitting unit is a self-luminous flat and/or flexible OLED unit. An OLED unit advantageously generates sufficient light in situ on its own so that advantageously separate remote light coupling may be dispensed with.

Preferably, the light-emitting unit is arranged to emit light in an entire light emission area and to form a 360° status display. Advantageously, both a flexible beaconing light conductor and a flexible, i.e. deformable OLED unit may be shaped into a beaconing emitter which irradiates light into all directions in space.

Preferably the light-emitting unit is arranged with at least part of its extension along a peripheral housing contour of the at least one housing, on at least one partial surface of the at least one housing and/or projecting from the at least one housing. Advantageously, in this way the machine for extracorporeal blood treatment can be provided with at least one predetermined luminous graphics.

Preferably, the light-emitting unit is guided with at least part of its extension on the inside of the machine for extracorporeal blood treatment along a transparent or opaque portion of a housing wall of the at least one housing and is arranged to irradiate output light through the transparent or opaque portion to the outside of the machine for extracorporeal blood treatment. Thus, for example, an anti-glare object or working illumination such as an illumination of connections or operating elements on the machine for extracorporeal blood treatment can be configured.

Of preference, the light-emitting unit covers at least part of a housing surface of the at least one housing or is embedded in at least part of the housing surface. The at least one housing may be a housing of a monitor connected to a base configuration of the machine for extracorporeal blood treatment.

Preferably the light-emitting unit includes a predetermined progression, line and/or area graph.

Preferably the light-emitting unit is arranged for emitting at least in portions polychromatic or over the full surface monochromatic light.

BRIEF DESCRIPTION OF THE DRAWINGS

The invention is best understood from the following detailed description when read in connection with the accompanying drawings. Included in the drawings are the following figures.

DETAILED DESCRIPTION OF PREFERRED EMBODIMENTS

Figure 1:
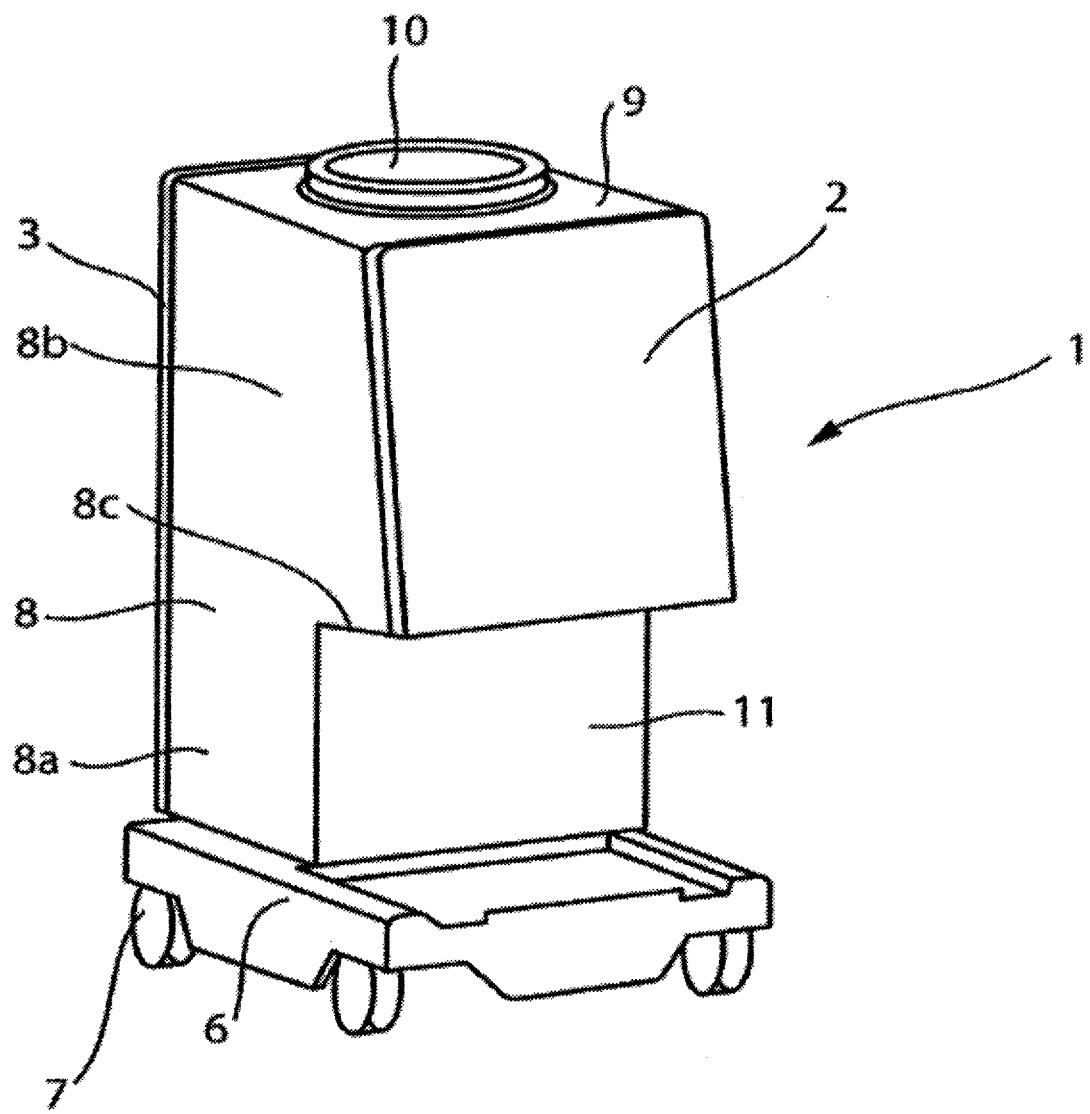
FIG. 1 shows in a simplified perspective view an apparatus housing of a dialyzer as a medical apparatus (machine) for extracorporeal blood treatment.

In the following description of figures, in the individual figures like or equally acting elements and/or components are denoted equally and/or with like reference numerals and expediently are not described in a redundant manner. In cases in which a subsequent embodiment functionally corresponds to at least one preceding embodiment, i.e. corresponding functions, arrangements and/or process or operating cycles are equally comprised, usefully only differences shall be discussed.

FIG. 1 shows in a simplified perspective view an apparatus housing of a dialyzer as a medical apparatus for extracorporeal blood treatment. In accordance with FIG. 1, the dialyzer includes a substantially self-supporting apparatus or machine housing 1 (hereinafter referred to as housing) in which a number of machine parts or machine components for carrying out blood treatment are arranged or can be arranged to functionally interact in a way known per se, such as control electronics, at least parts of the hydraulic system, pumps, heating units and, where necessary, tanks or bags for selected operating materials all of which are sufficiently known from prior art and therefore will not be represented or described in detail.

The housing 1 according to FIG. 1 may substantially include, for example, at least two side plates 8, a rear wall 3 configured at least partly as a pivoting door/cover, a hood 9 connecting the two side plates 8 (spaced in parallel) on the upper side, a bottom plate (for example as part of an apparatus base) 6 connecting the two side plates 8 on the bottom side and a front wall configured at least partly as pivoting door/cover 2. Further, a number of joint or hinge devices (not shown) may be provided at appropriate locations so as to enable the pivoting door/cover 2 and/or the rear wall 3 to be opened and closed.

A connecting base 10 on which an additional apparatus such as a monitor and/or an operating panel (not shown) may be mounted can be centrally formed integrally with the hood 9. The bottom plate 6 may include, at positions spaced in the circumferential direction of the housing, pivot points to which apparatus rollers 7 can be/are mounted which may form an internal (integrated) carriage of a mobile dialyzer together with the bottom plate 6. Alternatively, the bottom plate 6 may be placed on a separate carriage, for instance a roll cart, unless any apparatus rollers 7 are provided.

The two preferably one-piece side plates or side parts 8 spaced in parallel preferably may be adapted to be divided into two plate portions 8a, 8b spaced in height, i.e. into a lower portion 8a of smaller depth and an upper portion 8b of larger depth, comprising a projection 8c between the upper and lower portions. In the area of the lower portion 8a the two side plates 8 may be tightly connected via a front plate 11, for example may be welded or screwed stiffening the two side plates 8 in the transverse direction.

Equally, the hood 9 and preferably also the apparatus base and, respectively, the bottom plate 6 may be fixed to the upper and lower edges of the two side plates 8, for instance welded to be stiffening over at least parts of the edge length. In this way, the two side plates 8, the hood 9, the bottom plate 6 and the front plate 11 are adapted to provide a torsion-resistant housing 1 the interior of which on the rear side is completely accessible and on the front side is accessible at least in the area of the upper portion 8b.

Figure 2:
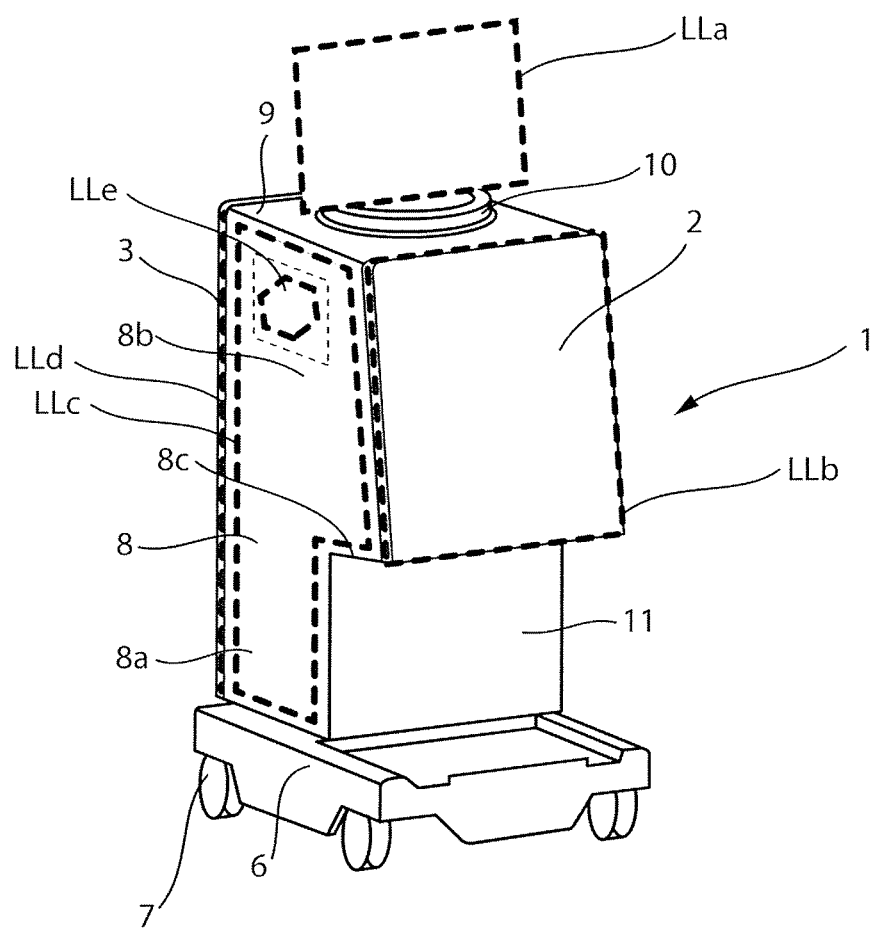
FIG. 2 shows the apparatus housing according to FIG. 1 comprising a light conductor as light-emitting unit according to a first preferred embodiment of the dialyzer including the light-emitting unit.

FIG. 2 illustrates the apparatus housing according to FIG. 1 comprising a light conductor as light-emitting unit according to a first preferred embodiment of the dialyzer comprising a light-emitting unit.

In the first embodiment shown in FIG. 2, at least one light (wave) conductor or light conductor of predetermined length is used as light-emitting unit for defined illumination inside and/or outside the dialyzer.

The light conductor is an optically transparent element preferably flexible in the longitudinal direction, such as a (glass) fiber or a bundle of said fibers, a pipe or a rod which is designed to convey light and may be made from glass or especially for illumination purposes preferably partly or completely from polymeric material adapted to be flexibly laid such as polymethylmethacrylate (PMMA) or polycarbonate (PC), for example.

In a first embodiment of the light conductor, the latter can be configured so that light conduction is achieved either by total reflection by an interface of its periphery due to a lower refractive index of the medium surrounding the light conductor or by silvering the interface. In this first embodiment, at a first end of the light conductor on the end face light can be coupled in via a luminaire, for example at least one light-emitting diode, preferably at least one bright or super-bright LED, or other suitable light sources, the coupled light is conveyed through the light conductor at low loss and exits again at a second end of the light conductor.

In a second embodiment of the light conductor, the latter can be configured (activated) with surface modifications, for example by a defined modification at a predetermined position or else along the entire length, so that light coupled in at modified positions at the first end is emitted again via the shell. In other words, in this second embodiment light is coupled out by partial interruption of the total reflection transversely to the conveying direction of the light and therefore, in the case of an active light source, the light conductor emits light also along its longitudinal extension, wherein one or more illumination points can be tapped off along the laying path of a flexible light conductor supplied by a light source. The light may be output on all sides radially or all around or on a side of the light conductor being diametrically opposed to a varied position through the cover layer. A modified position, for example a predetermined damage, may be produced, for instance, by specifically roughening a predetermined peripheral area of the light conductor e.g. by mechanically abrasive machining.

In the first example, the afore-mentioned first and second embodiments enable illumination, lighting and/or signalizing dependent on the apparatus condition or the status, respectively, of both the dialyzer and the environment thereof to be provided. On the one hand, for example a light conductor LLa, LLb, LLc, LLd may be arranged corresponding to a peripheral housing contour. The light conductor LLa, LLb, LLc, LLd can be flexibly laid, i.e. it can be guided starting from a light coupling position at an appropriate location inside the housing 1 to a housing wall and there can be inserted or immersed, for instance, into circumferential recesses (grooves) at housing parts (LLa, LLb, LLc, LLd), can be arranged with retaining elements in the form of a contour or an edge on the surface (LLa, LLb, LLc, LLd) extending with optional light conductor graphics on the inside behind transparent wall portions (LLe), and/or can be provided, in extension where necessary, as a free shape protruding from a housing wall (not shown). The afore-mentioned examples of arrangement moreover can be combined with each other. In this respect, there is not particular restriction as long as minimum bending radii of the light conductor can be observed, for example.

Thus it is possible, for example, as schematically indicated in FIG. 2, to illuminate a frame of a monitor or operating panel of the dialyzer disposed on the upper side at the periphery thereof and/or on the end face with a light conductor LLa corresponding to a circumferential housing contour, and/or to guide a light conductor along the periphery of the connecting base 10, and/or to guide a light conductor LLb along the peripheral contour of the door/cover 2, and/or to embed light conductor graphics LLc into at least one of the housing walls, for example into a side wall 8, and/or to guide light conductor graphics LLe behind a transparent or, respectively, opaque portion of at least one of the housing walls so as to shine through, and/or to guide a light conductor LLc along particular housing contours only in a visible and light outputting manner, respectively, and otherwise in a hidden manner without any light output, respectively.

The flexible light conductor LLa, LLb, LLc, LLd, LLe may moreover interact with coupling light sources such as, e.g., light-emitting diodes in different colors and intensities. In this way, both gentle ambient illuminations and lightings and illuminations of strong light intensity can be realized. Examples of application to a dialyzer may be, for example, an emergency light, a night luminaire, a handle illumination, a connection illumination, an edge and contour lighting, a working place illumination, a service light, hazard notes, a signal light, an object lighting, for example also moving along dependent on the operating cycle and/or varying in color and/or intensity, and the like. It is possible, in a comparable manner, to achieve partial lighting by a laterally circumferential light conductor.

Figure 3:
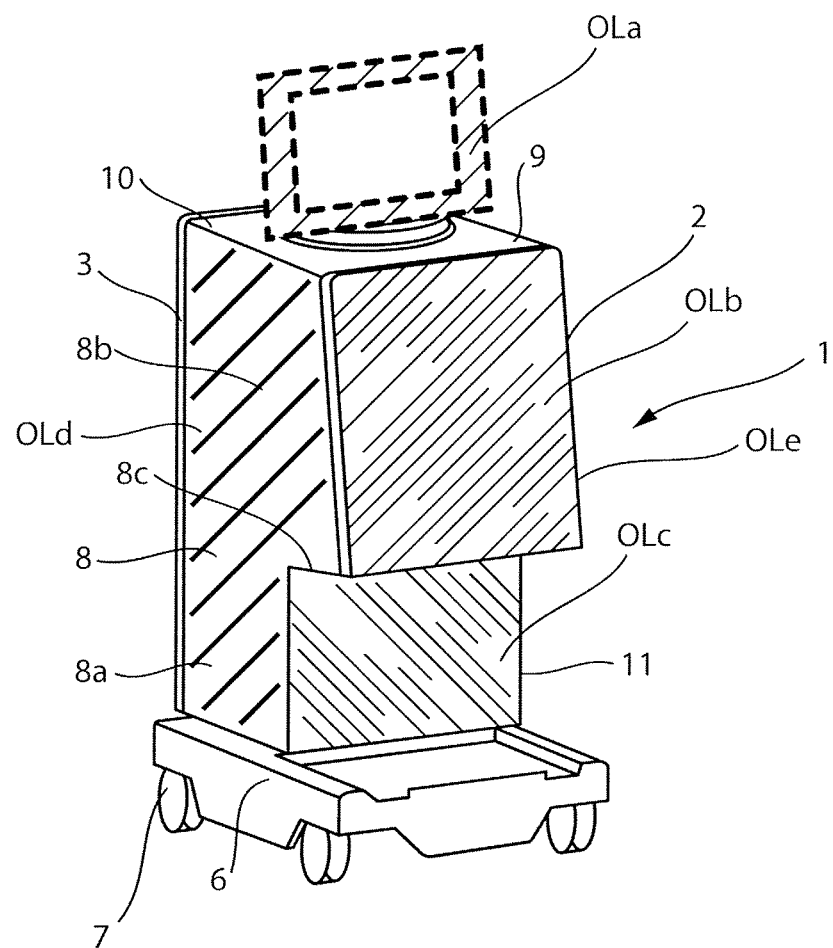
FIG. 3 shows the apparatus housing according to FIG. 1 comprising an OLED unit as light-emitting unit according to a second preferred embodiment of the dialyzer comprising a light-emitting unit.

FIG. 3 illustrates the apparatus housing according to FIG. 1 comprising an OLED unit OLa, OLb, OLc, OLd, OLe as light-emitting unit in accordance with a second preferred embodiment of the dialyzer comprising a light-emitting unit.

OLED is known per se as "organic light-emitting diode" and as such may be considered to be a particular type of LED that requires no backlight, works through an electroluminescent layer and is made from compound film acting like a semiconductor, with the film being inserted between two different electrodes. The first electrode appears to be transparent.

Just as in the first embodiment, it is possible in the second embodiment to configure and achieve all of the light conducting and/or lighting variations described with respect to the light conductor LLa, LLb, LLc, LLd, LLe according to the first embodiment with the OLED unit OLa, OLb, OLc, OLd, OLe. In FIG. 3 a flat OLED unit is provided on a (partial) monitor surface (OLa) and/or a (partial) housing surface (OLb, OLc, OLd, OLe) in a schematically exemplified manner. When the OLED unit OLa, OLb, OLc, OLd, OLe is appropriately dimensioned, a housing surface can be fully lightened.

In this case, preferably a possibly multi-part AMOLED or OLED surface module shaped or composed according to surface graphics, for example, may be used as a flat homogeneously luminous area which may be fixed to have a construction height within the millimeter range to less than 1 mm for example resting on the housing surface or may be embedded in the same. Due to the self-luminous resilient and flexible characteristics of the OLED unit OLa, OLb, OLc, OLd, OLe in this case, as the entire OLED unit is adapted to be luminous, also 360° status displays can be configured.

It is noted that in the same dialyfzer a flexible light conductor according to the afore-mentioned first embodiment and an OLED unit according to the afore-mentioned second embodiment may be disposed repeatedly and in combination, where appropriate with different coloring and/or light intensity in each case, and may be controllable jointly or else separately. Furthermore, automatic dimming capability, i.e. adjustable light intensity, for example depending on ambient light, of individual or all light-emitting units may be provided to be controlled manually, depending on therapy or operating conditions and/or sensor-controlled.

In the foregoing, thus a dialyzer has been described which comprises at least one housing 1 for accommodating operational components of the dialyzer which is part of the dialyzer and a light-emitting unit LLa through LLe, OLa through OLe including no diffusion disk for displaying an operating and/or therapy condition of the dialyzer according to the principle of ambient light, with the light-emitting unit LLa through LLe, OLa through OLe being arranged in a predetermined sequence and/or with predetermined shaping on at least one portion of the housing 1. The light-emitting unit LLa through LLe, OLa through OLe is a flexible light conductor LLa through LLe including at least one end-face light coupling surface at a first end and at least one end-face light output surface at a second end or, alternatively, a self-luminous flat and/or flexible OLED unit LLa through LLe, OLa through OLe.

The light-emitting unit LLa through LLe, OLa through OLe allows for spatial separation of the light-generating position and the light-emitting position and exhibits high energy efficiency with simultaneously high degrees of freedom of the configuration and low cost. Due to the characteristic and the little space required, the light-emitting unit LLa through LLe, OLa through OLe can be easily laid even in the case of a narrow spatial situation and at locations that are difficult to reach. In favor of better maintainability, due to the afore-mentioned separation in space the light generation may be provided at a location which is easy to reach. The ambient light characteristic variable as to coloring and/or intensity improves the user's perception of the information to be transmitted.

It is understood that the invention is not limited to the afore-described examples, but that within the scope of protection defined by the following claims combinations of at least parts of said examples, modifications and equivalents may be resulting at the same time obviously to those skilled in the art.

The invention claimed is:

1. A machine for extracorporeal blood treatment, comprising:

at least one housing for accommodating operational components of the machine for extracorporeal blood treatment which forms part of the machine for extracorporeal blood treatment; and a light-emitting unit having no diffusion disk configured to produce ambient light to display at least one of an operating condition or a therapy condition of the machine for extracorporeal blood treatment, wherein the light-emitting unit is arranged on at least one portion of the housing other than an operating panel, and wherein the light-emitting unit is arranged in a predetermined shape, wherein the light-emitting unit is a flexible light conductor including at least one end-face light coupling surface at a first end and at least one end-face light output surface at a second end.

2. The machine for extracorporeal blood treatment according to claim 1, wherein the flexible light conductor includes at least one portion coupling out light in a radial direction along a longitudinal extension.

3. The machine for extracorporeal blood treatment according to claim 1, wherein the light-emitting unit is arranged to emit light in an entire light emission area and to form a 360° status display.

4. The machine for extracorporeal blood treatment according to claim 1, wherein at least part of an extension of the light-emitting unit is arranged at least one of along a circumferential housing contour of the at least one housing, on at least one partial surface of the at least one housing, or to project from the at least one housing.

5. The machine for extracorporeal blood treatment according to claim 1, wherein at least a part of an extension of the light-emitting unit is guided on the inside of the machine for extracorporeal blood treatment along a transparent or opaque portion of a housing wall of the at least one housing and is arranged for irradiating output light through the transparent or opaque portion to the outside of the machine for extracorporeal blood treatment.

6. The machine for extracorporeal blood treatment according to claim 1, wherein the light-emitting unit covers at least part of a surface of the at least one housing.

7. The machine for extracorporeal blood treatment according to claim 6, wherein the at least one housing is at least one of a housing of a monitor or an operating field connected to a base configuration of the machine for extracorporeal blood treatment.

8. The machine for extracorporeal blood treatment according to claim 1, wherein the light-emitting unit is embedded in at least part of a surface of the at least one housing.

9. The machine for extracorporeal blood treatment according to claim 8, wherein the at least one housing is at least one of a housing of a monitor or an operating field connected to a base configuration of the machine for extracorporeal blood treatment.

10. The machine for extracorporeal blood treatment according to claim 1, wherein the light-emitting unit exhibits at least one of a predetermined progression, line, or area graph.

11. The machine for extracorporeal blood treatment according to claim 1, wherein the light-emitting unit is arranged to emit at least in portions polychromatic or full-surface monochromatic light.

12. A machine for extracorporeal blood treatment, comprising:

at least one housing for accommodating operational components of the machine for extracorporeal blood treatment which forms part of the machine for extracorporeal blood treatment; and a light-emitting unit having no diffusion disk configured to produce ambient light to display at least one of an operating condition or a therapy condition of the machine for extracorporeal blood treatment, wherein the light-emitting unit is arranged on at least one portion of the housing other than an operating panel, and wherein the light-emitting unit is arranged in a predetermined shape, wherein the light-emitting unit is at least one of a self-luminous flat or self-luminous flexible OLED unit.

* * * * *